United States Patent [19]
Schmitz et al.

[11] Patent Number: 4,945,863
[45] Date of Patent: Aug. 7, 1990

[54] PROCESS FOR OPERATING A FUEL-BURNING ENGINE

[75] Inventors: Günter Schmitz; Hans-Jürgen Kutz, both of Aachen, Fed. Rep. of Germany

[73] Assignee: FEV Motorentechnik GmbH & Co. Kg, Fed. Rep. of Germany

[21] Appl. No.: 329,839

[22] Filed: Mar. 28, 1989

[30] Foreign Application Priority Data

Mar. 30, 1988 [DE] Fed. Rep. of Germany ....... 3810808
Dec. 8, 1988 [DE] Fed. Rep. of Germany ....... 3841264

[51] Int. Cl.$^5$ .................... F02D 41/00; F02D 41/14; G01N 27/22
[52] U.S. Cl. ................ 123/1 A; 73/61.1 R; 123/494
[58] Field of Search ............. 123/1 A, 478, 494, 575; 73/61.1 R; 324/61 R, 61 QS

[56] References Cited

U.S. PATENT DOCUMENTS

| | | | |
|---|---|---|---|
| 4,470,300 | 9/1984 | Kobayashi | 73/61.1 R X |
| 4,594,968 | 6/1986 | Degobert et al. | 123/1 A |
| 4,706,629 | 11/1987 | Wireland et al. | 123/1 A X |
| 4,770,129 | 9/1988 | Miyata et al. | 123/1 A |

OTHER PUBLICATIONS

Proceedings of the Fourth International Symposium On Alcohol Fuels Technology, dated Oct. 5, 1980.

*Primary Examiner*—Tony M. Argenbright
*Attorney, Agent, or Firm*—Watson, Cole, Grindle & Watson

[57] ABSTRACT

A process for operating a fuel-burning engine which uses a conventional fuel containing alcohol as an alternative fuel, the fuel-alcohol ratio being measured for the purpose of controlling the quantity of fuel to be added at any time, wherein the measurement of the alcohol ratio of the fuel fed in serves to pre-control the quantity of fuel fed in, whereas the air ratio is precision controlled via a lambda control.

12 Claims, 4 Drawing Sheets

PROCESS FOR OPERATING A FUEL-BURNING ENGINE

BACKGROUND OF THE INVENTION

This invention relates to a process for operating a fuel-burning engine which uses a conventional fuel containing an alternative fuel such as alcohol, the fuel-alcohol ratio being measured for the purpose of adjusting the quantity of fuel to be added at any time.

Given that the fossil energy reserves in the long run will be available only in limited quantities, in particular fuels obtained from crude oil, and given the increasing environmental protection requirements, alternative fuels, in particular methyl or ethyl alcohol, are being added to these fuels in increasing amounts. It should therefore be possible to arbitrarily refuel both with pure fuels and mixed fuels. With higher alcohol content it is necessary to know the blending ratio in order to attain optimal performance from the fuel-burning engine and to facilitate a precise proportioning of fuel adjusted to the operating conditions. The continuous determination of the alcohol content in the fuel, continuously fed to the fuel-burning engine in operation, presents special problems for automobile engines in which any possible blend can be attained by any arbitrary refueling of types of fuel.

The known optical processes are unsuitable for this purpose since they often utilize interface effects to determine the refraction index from which then the alcohol content can be inferred. Besides the difficulty of utilization in automobile engines, one drawback of such process is that the mix to be observed with a measurement must have a higher homogeneity, which must also be present especially at the boundary layer. The required precision has not been achieved with this process.

In the publication "Proceedings of the Fourth International Symposium on Alcohol Fuels Technology," Sao Paulo, Brazil, of October 5, 1980, the possibility of determining the alcohol content in fuels by means of dielectric measurements is described. However, due to the influences of temperature and conductance (induced by water content or other pollutants in the fuel), the process was rejected, since a reliable measurement suitable for fuel-burning engines could not be conducted.

SUMMARY OF THE INVENTION

It is an object of the present invention to provide a process for operating a fuel-burning engine of the aforementioned type that from the standpoint of equipment and circuits can be effected in a simple manner with high operating reliability and efficiency.

The invention provides that in a process of the aforementioned type the measurement of the alcohol content in the fuel fed in serves to pre-control the quantity of fuel fed in, while the air ratio is precision controlled by means of a known lambda control. Moreover, a better start and warm-up performance can be achieved for the fuel-burning engine, since the lambda control can start at higher exhaust temperatures. Thus, for example, an adaptive control can be realized in that the measuring cell or the measuring circuit and/or the evaluation circuit is adjusted by means of the correcting quantity of the lambda control.

According to one preferred embodiment the alcohol content of the fuel is determined in a shared circuit by measuring the capacitance and the conductance of a quantity of fuel accommodated in a measuring cell.

Furthermore, the shared circuit is oscillatory and its output frequency is evaluated as the measure of capacitance, whereby the quantity of fuel in the measuring cell or a portion thereof forms the dielectric of the capacitive part of the circuit.

The shared circuit can be a flip-flop circuit in which the quantity of fuel in the measuring cell or a portion thereof forms the dielectric of the frequency determining capacitor. The frequency of the flip-flop circuit can be evaluated to determine the capacitance of the circuit.

Special advantages can be achieved if the duty factor or one of the two switching conditions of the flip-flop circuit is evaluated to determine the conductance of the circuit.

Another preferred embodiment provides that prior to evaluating the measuring signal, a pre-processing is conducted in that the signal is converted by means of integration into a voltage corresponding to the duty factor.

It can also be expedient that prior to evaluating the measuring signal a pre-processing is conducted in that during the phase with high potential a counter counts up an external, higher frequency signal and during the phase with low potential it counts down such that the count at the end of the period is a measure for the duty factor.

The measured values can be scanned from the at least partially conductive wall of the measuring cell, which represents the first electrode, and from an at least partially conductive flow body, which represents the second electrode.

From the standpoint of construction and circuit technology it is expedient if the shared circuit and/or the evaluation of the measuring signals is/are integrated with a program and circuit into the fuel proportioning system.

Another preferred embodiment provides that the measuring cell be used as the frequency-determining member in a generator, whose frequency is changed by means of the parallel circuit of a known capacitor, whereby the two different frequencies are evaluated to determine the capacitance by means of computer or circuit technology. The frequency can also be changed by a switchable delay.

Other objects, advantages and novel features of the invention will become more apparent from the following detailed description of the invention when taken in conjunction with the accompanying drawings.

DETAILED DESCRIPTION OF THE DRAWINGS

Figure 1:
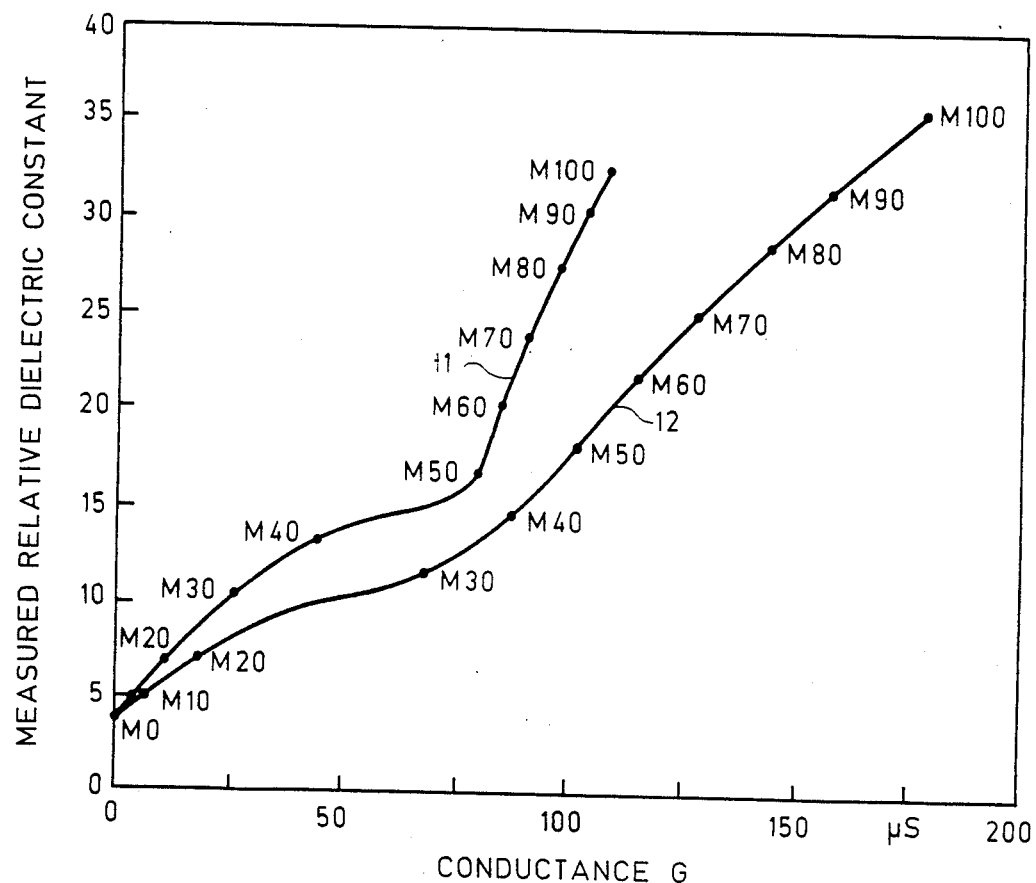
FIG. 1 is a diagram of the relative permittivity as a function of the conductance G based on the water content and the methanol content of the fuel.

In FIG. 1, the values of the dielectric measurement are plotted on the ordinate and the conductance G on the abscissa. Curve 11 shows the values of the dielectric measurement as a function of the proportion of methanol admixture with 0% water content in the fuel, whereas line 12 plots the corresponding values with 2.5% $H_2O$ content. The measured points for the variable percentages of methanol, ranging from 0% to 100% (MO to M100), are plotted on the curves.

It can be seen that with higher percentages of water specific dielectric values are measured at higher conductivities. With a combined measurement of conductance and relative permittivity empirically determined families of plotted curves of the type, shown in FIG. 1, allow for a correction of the dielectric measurement by means of determining the conductance.

By knowing the conductance the cross influences on the capacitance due to pollutants in the fuel can now be corrected. As FIG. 1 shows, a higher percentage of water in the fuel, for example, increases the capacitance. By measuring the conductance, this increase in the capacitance can be taken into consideratiion when the alcohol content is determined.

Figure 2:
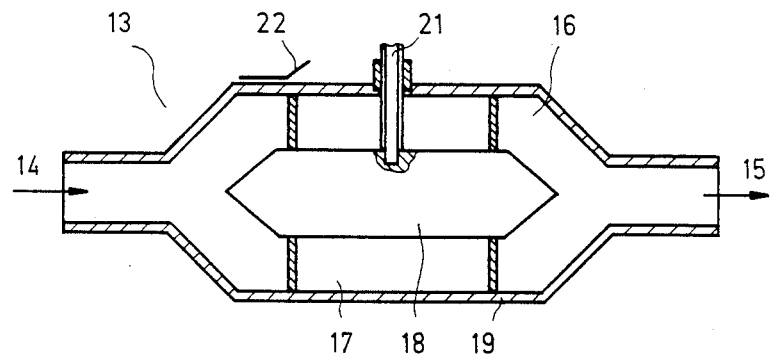
FIG. 2 is a preferred example of a measuring cell for carrying out the process according to the invention.

FIG. 2 shows a preferred embodiment of a measuring cell for carrying out the process of the invention. The fuel enters the measuring cell via in-flow 14, and it leaves the measuring cell via out-flow 15. In the areal presentation of FIG. 2, the fuel current divides into current paths 16 and 17, which are formed by a central cylinder 18. If the central cylinder 18 and the outer shell 19 conduct electricity partially or completely, these walls or parts of walls of the measuring cell can represent the electrodes of a measuring or evaluation circuit. Within the at least partially conductive wall of the measuring cell, which represents the first electrode, as a flow body the at least partially conductive central cylinder 18 is the second electrode.

The central cylinder 18 and the outer shell 19 form the actual precision capacitor, which encloses the measured volume. The corresponding values can be scanned at the connectors 21 and 22, and in particular both for the capacitance and for the conductance at the same electrodes. The scanned values are then fed into the shared circuit for further processing.

Figure 3:
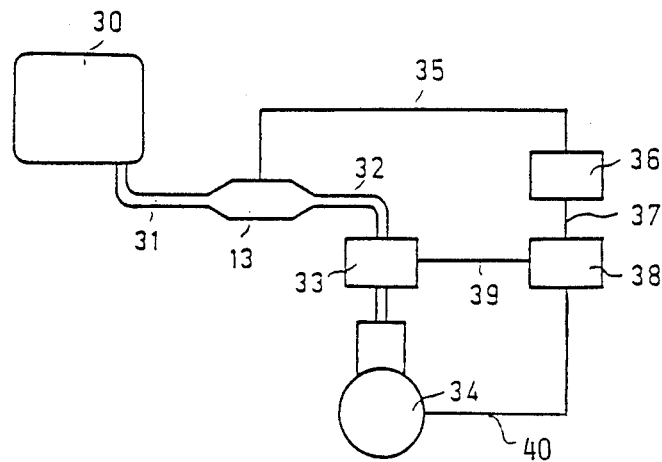
FIG. 3 is a schematic of the arrangement in order to apply the process of the invention for controlling or regulating a fuel-burning engine.

As evident from the schematic in FIG. 3, fuel mixed with alcohol travels from fuel tank 30 via a line 31 to the measuring cell 13 and from there via a line 32 to a proportioning device 33, which can be an injection pump with corresponding injection nozzles. The fuel is fed into the engine for burning by means of direct or indirect injection.

The values of the capacitance and conductance, scanned in the measuring cell 13, are fed via the measuring line 35 of a shared evaluation circuit or evaluation unit 36. Preferably the shared circuit 36 is oscillatory, and its output frequency can then be evaluated as the measure of the capacitance. In this oscillatory shared circuit 36 the quantity of fuel in the measuring cell 13 or a portion thereof is the dielectric of the capacitive part of the evaluation circuit 36.

The signals transmitted by the evaluation circuit 36 travel over a line 37 to an injection computer 38, and it controls proportioning device 33 via a line 39. Thus the mixing ratio evaluated in the evaluation unit 36 and measured in the measuring cell 13 is not operationally changed but rather the type of injection is changed depending on the measured and evaluated values.

An important feature is that the measurement of the alcohol content of the fed-in fuel serves to pre-control the injected quantity, whereas the air ratio is precision controlled by means of connection 40 via a known type of lambda control. Thus higher operating reliability and efficiency for operating the fuel-burning engine can be attained, and in particular in an especially simple manner with equipment and circuit technology.

Especially for automotive engines, when applying the process of the invention to injection fuel-burning engines, it may be suitable to integrate the shared circuit as the evaluation unit into the injection system by means of circuit and program technology. Moreover, the temperature of the fuel in the measuring cell 13 can also be specified and fed into the evaluation unit to compensate for the influence of temperature.

Special advantages can be attained if the shared circuit is a flip-flop circuit in which the quantity of fuel in the measuring cell forms the dielectric of the frequency-determining capacitor. Thus the frequency of the flip-flop circuit is preferably evaluated to determine the capacitance, while the duty factor of the flip-flop circuit can be evaluated to determine the conductance. Thus the effect is used that a capacitance change in the frequency-determining capacitor of a flip-flop circuit changes both the charging time and the discharging time of the capacitor and that a change in the conductance parallel to the capacitor with respect to the charging time and the discharging time changes in the opposite sense and thus the duty factor is also changed.

Thus the duty factor for a given capacitance represents a measure for the conductiveness; and the frequency or the cycle duration of the signal represents a measure for the capacitance with a cross-influence on the conductance. An additional circuit or circuit component can compensate for this cross-influence, for example, empirically or by means of computer or circuit technology.

Figure 4:
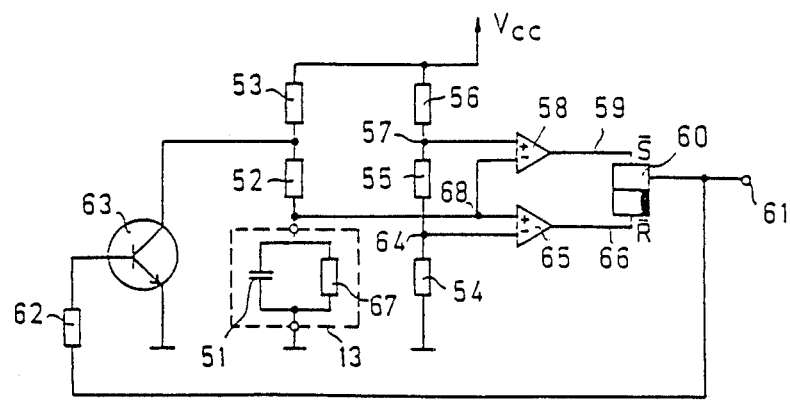
FIG. 4 shows a flip-flop circuit as the preferred embodiment of a circuit for carrying out the present process.

A preferred embodiment of a flip-flop circuit of the aforementioned type is shown in FIG. 4. The capacitance 51 of the measuring cell 13 is charged via resistors 52 and 53 by the supply voltage Vcc until a threshold voltage U1, which is formed by means of resistors 54, 55 and 56 at point 57, is overridden at comparator 58. Then the comparator output 59 goes "high" to "low level" and sets flip-flop 60, whose output 61 switches to "high level." Now a transistor 63, which initiates the discharging process of the capacitance 51 via the resistor 52, is switched on via resistor 62. If the voltage at the capacitance 51 drops now below the threshold value U2, which is formed at point 64 by means of resistors 54, 55 and 56, a comparator 65 switches its output 66 from "high" to "low level." Thus the flip-flop 60 is re-set; the transistor 63 switches into the high-impedance state, and the capacitance 51 is re-charged.

In order for the circuit, shown in FIG. 4, to function reliably even with high conductance, a mutual capacitance for direct current suppression can be installed between the resistor 52 and the capacitance 51 with conductive function 67 of the measuring cell 13, whereby the connection 68 with the comparators 58 and 65 must be between the resistance 52 and the mutual capacitance.

Other advantageous possibilities are available if prior to evaluating the mesuring signal, pre-processing is conducted, for example, in that the signal for determining the frequency goes through a dividing stage. This is especially expedient if the measured frequencies are in the megahertz range, whereas the reference frequency available for evaluation can be significantly lower.

A pre-processing can also be conducted before the measuring signal is evaluated by converting the signal by means of integration into a voltage corresponding to the pulse duty factor, since the duty is frequently very difficult to determine by signals having very high frequency, in particular in the megahertz range. In particular by these measures the evaluation is facilitated with a microprocessor.

Finally it can also be expedient that prior to the evaluation of the measuring signal a pre-processing is conducted in that during the phase with high potential ("high phase") of the flip-flop circuit a counter counts up an external, higher frequency signal and during the phase with low potential ("low phase") it counts down, in such a manner that the count at the end of the period represents a measure for the duty factor. Thus high precision can be attained with surveyable switching conditions.

Figure 6:
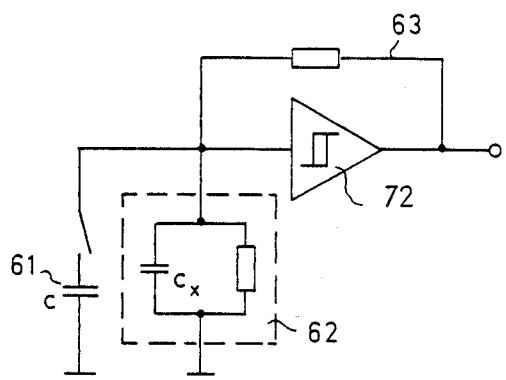
FIG. 6 is a schematic of an arrangement for changing the frequency by means of the parallel circuit of a known capacitor.

According to FIG. 6, in one of the preferred embodiments the measurement is performed in two phases, whereby in the second measurement a defined capacitance C, shown at 61, is switched parallel to the measuring cell capacitance Cx, shown at 62. Thus two different frequencies are obtained whose evaluation yields a statement about the capacitance. In the simplest case the resulting formula is: $f_2/f_1 = C_x/(C_x + C)$.

Figure 5:
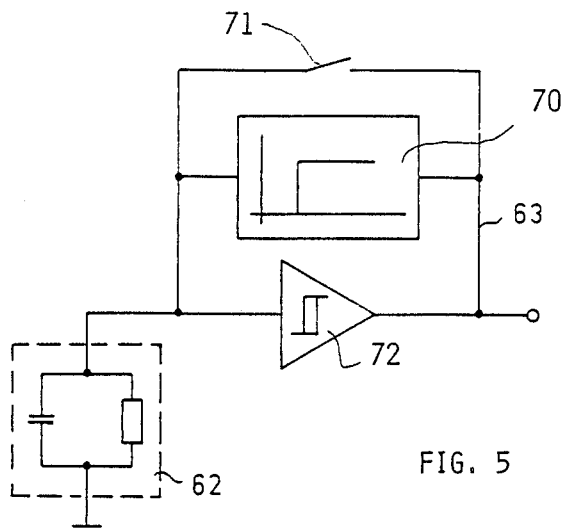
FIG. 5 is a schematic of the arrangement for changing the frequency by means of a switchable delay.

With respect to series production there are special advantages if instead of the switched capacitance a switchable delay is inserted, for example, into the feedback path 63, as shown in FIG. 5. Similar to a parallel circuit of the capacitance, it lowers the frequency so that the frequencies can be evaluated in the same manner. A delay member 70 by means of which a delay of defined length can be brought about is in the feedback path 63. When the switch 71 is closed, the delay member 70 is switched off, whereas when the switch 71 is opened, it is re-activated. Two threshold values of the capacitor voltage are monitored by means of Schmidt trigger 72 so that the capacitor is continuously charged and discharged.

The invention is not restricted to blends of alcohol with conventional carburetor fuels but is also applicable to other kinds of fuel blends whose components have different stoichiometric air requirements or different thermal values.

Obviously, many other modifications and variations of the present invention are made possible in the light of the above teachings. It is therefore to be understood that within the scope of the appended claims the invention may be practiced otherwise than as specifically described.

What is claimed is:

1. A process for operating a fuel-burning engine which uses a conventional fuel containing alcohol as an alternative fuel, comprising the steps of measuring the fuel-alcohol ratio for controlling the quantity of fuel to be injected during engine operation, and determining the alcohol content of the fuel-alcohol ratio in a shared circuit by measuring the capacitance and the conductance of a quantity of fuel accommodated in a measuring cell.

2. The process according to claim 1, wherein the shared circuit is oscillatory, and evaluating the output of the shared circuit as a measure of the capacitance, whereby the quantity of fuel in at least a portion of the measuring cell forms the dielectric of the capacitance part of the circuit.

3. The process according to claim 1, wherein the shared circuit comprises a flip-flop circuit in which the quantity of fuel in at least a portion of the measuring cell forms the dielectric of the frequency-determining capacitor.

4. The process according to claim 3, comprising evaluating the frequency of the flip-flop circuit to determine the capacitance of the circuit.

5. The process according to claim 3 or 4, comprising evaluating the duty factor or one of the two switching conditions of the flip-flop circuit to determine the conductance of the circuit.

6. The process according to claim 5, comprising conducting a pre-processing prior to the evaluation of the measuring signal such that the signal is converted by integrating into a voltage corresponding to the duty factor.

7. The process according to claim 5, comprising conducting a pre-processing prior to the evaluation of the measuring signal such that during the phase with high potential counting up an external, high frequency signal is carried out by a counter, and counting down is carried out by the counter during the phase with low potential such that the count at the end of the period represents a measure of the duty factor.

8. The process according to claim 1, comprising scanning measured values at at least a partially conductive wall of the measuring cell which represents a first electrode, and scanning measured values at at least a partially conductive flow body which represents a second electrode.

9. The process according to claim 1, comprising integrating the shared circuit and/or the evaluation of the measuring signals into the fuel proportioning system.

10. The process according to claim 1, comprising employing the measuring cell as a frequency-determining member in a generator whose frequency is changed by means of a parallel circuit of a capacitor, evaluating the two different frequencies to determine the capacitance by means of a computer or a circuit.

11. The process according to claim 10, comprising effecting the frequency change by a switchable delay.

12. The process according to claim 1, wherein the measurement of said ratio of the fuel fed into the engine serves to pre-control the quantity of fuel fed in, and further comprises precision controlling the engine air ratio by means of a lambda control.

* * * * *